United States Patent
Panin et al.

(10) Patent No.: US 10,226,444 B2
(45) Date of Patent: Mar. 12, 2019

(54) TISSUE REPAIR OF THE NASAL MUCOSA AND TREATMENT OF RHINITIS WITH ALPHA-TOCPHEROL COMPOSITIONS

(71) Applicant: BIO.LO.GA. S.R.L., Conegliano (TV) (IT)

(72) Inventors: Giorgio Panin, Rovigo (IT); Domenico Testa, Caserta (IT); Germano Guerra, Altavilla Silentina (IT)

(73) Assignee: BIO.LO.GA. S.R.L., Conegliano (TV) (IT)

( * ) Notice: Subject to any disclaimer, the term of this patent is extended or adjusted under 35 U.S.C. 154(b) by 0 days.

(21) Appl. No.: 15/512,755

(22) PCT Filed: Oct. 2, 2015

(86) PCT No.: PCT/EP2015/072796
§ 371 (c)(1),
(2) Date: Mar. 20, 2017

(87) PCT Pub. No.: WO2016/062522
PCT Pub. Date: Apr. 28, 2016

(65) Prior Publication Data
US 2017/0290799 A1    Oct. 12, 2017

(30) Foreign Application Priority Data
Oct. 22, 2014   (IT) .............................. MI2014A1819

(51) Int. Cl.
*A61K 31/355*    (2006.01)
*A61K 47/32*     (2006.01)
(Continued)

(52) U.S. Cl.
CPC .......... *A61K 31/355* (2013.01); *A61K 9/0043* (2013.01); *A61K 47/32* (2013.01); *A61K 47/44* (2013.01)

(58) Field of Classification Search
CPC ...... A61K 31/355; A61K 47/32; A61K 47/44; A61K 9/0043
See application file for complete search history.

(56) References Cited

U.S. PATENT DOCUMENTS 4,364,945 A    12/1982  Whittle
2010/0055152 A1  3/2010  Wahi
(Continued)

FOREIGN PATENT DOCUMENTS

FR    2981273 A1    4/2013
WO    1997045098 A2  12/1997
WO    2000002554 A1   1/2000

OTHER PUBLICATIONS

Truthinaging document (Mar. 2009, downloaded from the internet on Apr. 11, 2018, URI: https://web.archive.org/web/20111022132308/ https://www.truthinaging.com/ingredients/hydrogenated-polydecene.*

(Continued)

*Primary Examiner* — Savitha M Rao
(74) *Attorney, Agent, or Firm* — Silvia Salvadori, P.C.; Silvia Salvadori

(57) ABSTRACT

Composition for topical application, for use in increasing the trophism of nasal mucosa, comprising an ester of vitamin E with a carboxylic acid of formula R—COOH, in which R is an alkyl radical having 1 to 19 carbon atoms, or an alkenyl or alkynyl radical having 2 to 19 carbon atoms, and an oily vehicle; such composition can be used for the treatment of chronic atrophic rhinitis and for obtaining tissue repair of the nasal mucosa following nasal and sinus surgery.

14 Claims, 1 Drawing Sheet

(51) Int. Cl.
*A61K 47/44* (2017.01)
*A61K 9/00* (2006.01)

(56) References Cited

U.S. PATENT DOCUMENTS

2011/0165094 A1* 7/2011 Panin .................... A01N 49/00
                                                          424/43
2013/0028961 A1 1/2013 Vajdy et al.

OTHER PUBLICATIONS

Office Action dated Apr. 3, 2017 for U.S. Appl. No. 15/325,890 owned by same applicant.
Anonymous et al, "El blog de Arapiles Farmacia: VEA que puede hacer por su piel", Nov. 25, 2013, retrieved from the Internet URL:http://arapilesfarmacia.blogspot.nl/2013/11/vea-que-puede-hacer-por-su-piel.html.
Hildebrand T., et al., "Rhinitis sicca, dry nose and atrophic rhinitis: a review of the literature", European Archives of Oto-Rhino-Laryngology; and Head and Neck, Springer, Berlin, DE, vol. 268, No. 1, Sep. 29, 2010, pp. 17-26.
International Preliminary Report on Patentability of PCT/EP2015/072796 dated Sep. 23, 2016 and response to written opinion.
Search Report of PCT/EP2015/072796 dated Dec. 21, 2015.
Written Opinion of PCT/EP2015/072796 dated Dec. 21, 2015.

\* cited by examiner

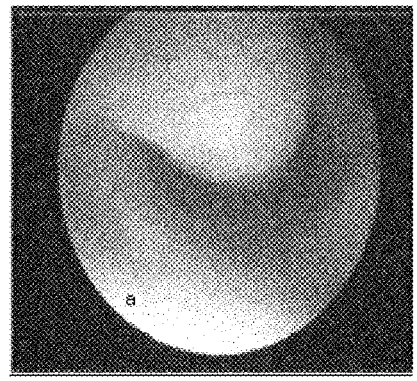
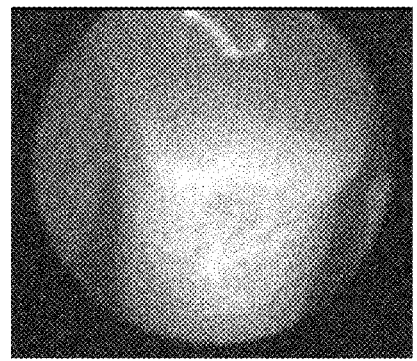
Fig. 1a    Fig. 1b
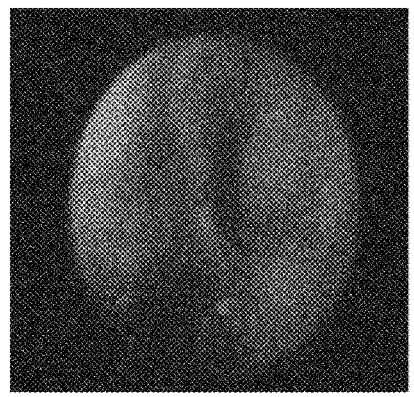
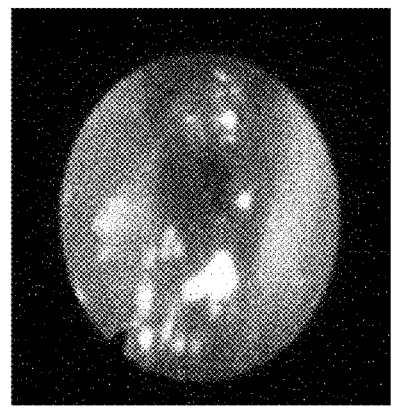
Fig. 2a    Fig. 2b

TISSUE REPAIR OF THE NASAL MUCOSA AND TREATMENT OF RHINITIS WITH ALPHA-TOCPHEROL COMPOSITIONS

This application is a U.S. national stage of PCT/EP2015/072796 filed on 2 Oct. 2015, which claims priority to and the benefit of Italian Application No. MI2014A001819, filed on 22 Oct. 2014, the contents of which are incorporated herein by reference in their entireties.

FIELD OF APPLICATION

The present invention refers to the pharmaceutical industry field. In particular, the invention regards a pharmaceutical composition for use in increasing trophism of nasal mucosa for example in case of chronic atrophic rhinitis or following nasal and sinus surgery.

PRIOR ART

Chronic atrophic rhinitis, which is divided into Primary Chronic Athrophic Rhinitis and Secondary Chronic Atrophic Rhinitis, represents a disease of major interest in otology both due to chronic modifications of the nasal mucosa and possible complications caused by infections undergone by a deteriorated and metaplastic mucosa.

Symptoms of atrophic rhinitis include a feeling of obstruction of the nasal septum, as a consequence of the atrophy of the nerve endings, burning, cough and disorder of the sense of smell.

The therapy, which is currently used for atrophic rhinitis, although it displays only poor efficacy, essentially consists in cleansing the nasal cavities by washing using isotonic and hypertonic saline solutions to prevent or limit the formation of crusts. Nasal ointments based on panthenol, oily solutions like sesame oil or vitamin A-based oil, as well as hyaluronic acid- or panthenol-based aqueous sprays are also used.

Patent application WO97/45098 discloses the use of tocopherol acetate as the only ingredient of a medicament for the treatment of atrophic rhinitis. However, tocopherol acetate—as it is—is not easy to apply on the nasal mucosa due to its high viscosity.

Patent application WO 00/02554 discloses the use of tocopherol acetate as the only ingredient of a medicament for the treatment of encrusted rhinitis resulting e.g. from adenoidectomy, which is not an intervention of nasal and sinus surgery.

FR 2 981 273 discloses topical formulations for the treatment of mucosae, comprising i.a. 40-85% of tocopherol acetate, 10-60% of a macerate of calendula flowers in musk rose vegetable oil, retinol palmitate, ascorbyl palmitate, ubiquinone and lactobacilli. It is only described the application of this formulation in the treatment of the oral and vaginal mucosa.

Deterioration of the trophism of the nasal mucosa also occurs in another condition, namely following nasal and sinus surgery. Nasal respiratory deficit is mainly due to two factors: a mucous factor, represented by the hypertrophy of the inferior turbinate and the medium turbinate accessorily, and a structural factor, constituted by morphological/structural alterations of the nasal septum and pyramid. The surgical correction of a nasal obstruction should consider the frequent coexistence of the two aforementioned factors in the etiology of the obstruction and this leads to the frequent need for a "septum/turbinate" surgery.

The average healing period of the tissues following nasal and sinus surgery is about 20 days and during this period, constant cleaning of the nasal cavities with hypertonic saline solutions and topical instillation of medicated oils are necessary to facilitate a correct tissue repair, with the aim of avoiding the stagnation of blood clots and mucus, which could lead to post-surgery complications (septum and turbinate synechiae, fibrous tissue affecting the turbinate or the nasal floor etc.).

SUMMARY OF THE INVENTION

The object of the present invention is to provide a medicament for increasing the trophism of nasal mucosa.

In a first aspect, the object was to obtain such increase of the trophism of nasal mucosa following nasal and sinus surgery.

In a second aspect, the object was to obtain such increase of the trophism of nasal mucosa in case of chronic atrophic rhinitis.

The aforementioned objects were obtained by providing a composition for topical application, for increasing the trophism of nasal mucosa, comprising an ester of vitamin E with a carboxylic acid of formula R—COOH, in which R is an alkyl radical having 1 to 19 carbon atoms, or an alkenyl or alkynyl radical having 2 to 19 carbon atoms, and an oily vehicle.

According to an aspect of the present invention, such composition is intended to be used in the tissue repair of the nasal mucosa following nasal and sinus surgery.

According to another aspect of the present invention, such composition is intended to be used in the treatment of chronic atrophic rhinitis.

Preferably the aforementioned composition does not comprise any other ingredient besides the aforementioned ester of vitamin E and the aforementioned oily vehicle.

By the term "vitamin E" the following compounds are meant: d-α-tocopherol, a mixture of the two enantiomers d and l of α-tocopherol, a mixture of other tocopherols (β, γ, δ, ε, ζ, η) or tocotrienols.

Preferably, the aforementioned ester is vitamin E acetate, n-propionate or linoleate.

Particularly preferred is the use of vitamin E acetate, in particular alpha-tocopheryl acetate.

Preferably the composition comprises from 3% to 80%, conveniently from 5% to 40% and advantageously from 10% to 30% by weight of the above mentioned ester of vitamin E on the total weight of the composition.

Preferably the oily vehicle is selected from the group comprising (INCI name is indicated in parentheses) hydrogenated polyisobutene (Hydrogenated Polyisobutene), hydrogenated polydecene (Hydrogenated Polydecene), mixtures of hydrogenated polyisobutene and/or hydrogenated polydecene with hydrogenated polyolefins, in particular hydrogenated $C_6$-$C_{14}$ polyolefins (Hydrogenated $C_6$-$C_{14}$ Polyolefins), caprylic/capric glyceride (Caprylic/Capric Triglyceride), olus oil (Olus Oil), baobab oil (Adansonia Digitata Oil), baobab seed oil (Adansonia Digitata Seed Oil), coco caprylate/caprate (Coco-Caprylate/Caprate), olive squalane (Olive Squalane), olive squalene (Olive Squalene), sunflower oil (Sunflower (Helianthus Annus) Seed Oil), jojoba oil (Simmondsia Chinensis Oil), coco caprylate (Coco-Caprylate), isononyl isononanoate (Isononyl Isononanoate), cyclopentasiloxane (Cyclopentasiloxane), and mixtures thereof.

A particularly preferred vehicle is constituted by hydrogenated polydecene.

A particularly preferred composition consists of alpha-tocopheryl acetate and hydrogenated polydecene.

Advantageously, such composition consists of alpha-tocopheryl acetate 10-30% and hydrogenated polydecene 70-90%.

The invention also refers to an ester of vitamin E with a carboxylic acid of formula R—COOH, in which R is an alkyl radical having 1 to 19 carbon atoms, or an alkenyl or alkynyl radical having 2 to 19 carbon atoms for use in the tissue repair of the nasal mucosa following nasal and sinus surgery.

Preferably the ester of vitamin E for the use in question is vitamin E acetate, conveniently alpha-tocopheryl acetate.

All percentages indicated in the present application shall be deemed, unless otherwise indicated, as percentages by weight on the total weight of the composition.

BRIEF DESCRIPTION OF THE DRAWINGS

FIG. 1a is a rhino-fiberscopic image of the right inferior turbinate of a patient suffering from primary atrophic rhinitis prior to the treatment with the product VEA® Oris.

FIG. 1b is a rhino-fiberscopic image of the right inferior turbinate of the same patient of FIG. 1a, after three months of treatment with the VEA® Oris product.

FIG. 2a is a rhino-fiberscopic image of the nasal mucosa of a patient of group A of the clinical trial on patients subjected to septoplasty, inferior turbinectomy and anterior and posterior ethmoidectomy interventions as described hereinafter.

FIG. 2b is a rhino-fiberscopic image of the nasal mucosa of a patient of group B of the clinical trial on patients subjected to septoplasty, inferior turbinectomy and anterior and posterior ethmoidectomy interventions as described hereinafter.

DETAILED DESCRIPTION

Over the years, the Applicant has been producing a spray preparation based on alpha-tocopheryl acetate, sold under the name VEA® Oris (alpha-tocopherylacetate 14% and hydrogenated polydecene 86%), for application to the mucosa of the oropharyngeal cavity, having an emollient and protective action. Considering the favorable effects observed in the prevention and treatment of pharyngitis, which exceed the plausible expectations from a mere emollient action on the mucosa, and also considering the ease of application of such spray preparation, the Applicant thought of verifying whether such product also had a favorable effect on the nasal mucosa of patients suffering from chronic atrophic rhinitis.

It was actually observed that VEA® Oris exerts a therapeutic action over chronic atrophic rhinitis, in particular primary atrophic rhinitis, as it will appear from the trial results described hereinafter.

Clinical Trial 1

13 patients (9 women and 4 men), aged between 34 and 70 years (mean age 50.23) who had dry nose feeling and hyposmia, almost always associated with nasal respiration difficulties, were recruited in the period comprised between September 2013 and March 2014.

The patients were subjected to an accurate anamnesis to exclude possible patients affected by secondary atrophic rhinitis (SAR). Patients who had previously been subjected to nasal-sinus surgery, patients using vasoconstrictors and/or inhalers for therapeutic purposes and patients who tested positive to allergometric skin and serum tests were also excluded from the trial.

The utilized treatment schedule provided for the administration of VEA® ORIS spray through the nose according to the following doses: 2 puffs per nostril 3 times/day, for 3 months.

The observation stage after treatment with VEA® ORIS provided for endoscopic clinical observation, clinical and functional evaluation through rhinomanometry and the mucociliary clearance test.

From a symptomatology point of view, all patients revealed a considerable improvement of the dry nose feeling and perception of the nasal aerial flow (remission of the paradoxical nasal obstruction feeling).

The endoscopic observation allowed to observe increased hydration and blood supply of the nasal mucosa, as observable from the rhino-fiberscopic images of FIGS. 1a and 1b: FIG. 1a shows that the atrophic mucosa has a white-yellowish color while FIG. 1b shows considerable improvement of the trophism of the mucosa, which looks pinkish and well perfused at the end of the treatment.

The basal rhinomanometric assessment revealed an improvement of the nasal respiratory functionality due to increase of the nasal flow and reduction of resistance.

The mucociliary clearance test, after treatment with VEA® ORIS, revealed a reduction of the average transit time by 17 min.

Clinical Trial 2

The favorable effect of VEA® ORIS on trophism of nasal mucosa was also confirmed in the treatment of the nasal mucosa following nasal and sinus surgery.

The activity of VEA® ORIS was also tested in a therapeutic protocol administered to patients subjected to septoplasty, inferior turbinectomy and anterior and posterior ethmoidectomy interventions, with the aim of evaluating its re-epithelizing action and possible reduction in formation of serohematic crusts.

44 patients (25 men (M) and 19 women (F)) aged between 22 and 43 years (average age about 34.1), were recruited and divided into 2 groups:

Group A: 21 patients (13M and 8F) 15 of whom (10M and 5F) with deviated nasal septum associated to hypertrophy of the inferior turbinates and 6 (3M and 3F) suffering from chronic ethmoidal sinusitis;

Group B: 23 patients (19M and 4F) 12 of whom (11M and 1F) with deviated nasal septum associated with hypertrophy of the inferior turbinates and 11 (8M and 3F) suffering from chronic ethmoidal sinusitis.

The deviated nasal septum with hypertrophy of the inferior turbinates was treated with submucosal resection of the nasal septum and bilateral inferior turbinectomy; chronic ethmoidal sinusitis with anterior and posterior ethmoidectomy in FESS (functional endoscopic sinus surgery).

The post-surgery pharmacological treatment provided for the following schedule:

Group A: hypertonic saline solution (2 puffs per nostril 8/10 times a day for 10 days) associated with VEA® ORIS spray (2 puffs per nostril 3 times per day) for 20 days.

Group B: hypertonic saline solution (2 puffs per nostril 8/10 times a day for 10 days) associated with niaouli oil (2 applications per nostril 3 times a day) for 20 days.

The clinical controls were carried out after 7 days, after 15 days, after one month and after 3 months from the surgery; the clinical evaluation provided for fiberoptic rhinoscopy, rhinomanometry and Nasal Symptom Score (NSS).

After the first 15 days, there was observed a reduction in the production of crusts for patients of group A with respect to those of group B, with a nasal mucosa which started recovering its trophism.

FIG. 2a, regarding a patient of group A, actually shows low presence of serohematic crusts and a re-epithelization already at an advanced stage while FIG. 2b, regarding a patient of group B, shows the presence of numerous serohematic crusts in the nasal cavity.

The control after 1 month revealed the following:

patients of group A had good trophism of the nasal mucosa without crusts with respect to patients of group B which revealed a nasal cavity not entirely clear and a still partially de-epithelialized mucosa;

patients of the group A revealed a good NSS score equivalent to 8 (average score) with respect to patients of group B, who revealed an average score of 5.

At the endoscopic clinical control after 3 months, patients of group B revealed similar results as those attained by patients of group A after 1 month.

The post-surgery treatment after nasal sinus surgery has as its rationale the tissue healing and the most complete functional recovery, thus reducing the healing times; for this purpose, the use of VEA® ORIS revealed to be valid and more efficient with respect to the therapeutic protocol used in the control group.

In addition, the following formulations were prepared:

| 1) | |
|---|---|
| Alpha-tocopheryl linoleate | 14% |
| Hydrogenated polydecene | 86% |

| 2) | |
|---|---|
| Alpha-tocopheryl acetate | 10% |
| Hydrogenated polyisobutene | 90% |

| 3) | |
|---|---|
| Alpha-tocopheryl acetate | 25% |
| Olus Oil | 75% |

A preliminary trial of the three aforementioned formulations (in form of nasal spray) on three respective groups of five patients diagnosed with primary atrophic rhinitis, in the same trial conditions of the aforementioned clinical trial 1, provided results comparable with those obtained in the test with the VEA® Oris product.

The aforementioned three formulations were also tested on three respective groups of five patients, 3 of whom with deviated nasal septum associated with hypertrophy of the inferior turbinates and 2 suffering from chronic ethmoidal sinusitis, all subjected to septoplasty, inferior turbinectomy and anterior and posterior ethmoidectomy interventions, in the same trial conditions of clinical trial 2. The obtained results are comparable with those obtained in the test with VEA® Oris.

The invention claimed is:

1. A method of obtaining tissue repair of the nasal mucosa following nasal and sinus surgery, said nasal and sinus surgery being selected from the group consisting of septoplasty, inferior turbinectomy, anterior ethmoidectomy and posterior ethmoidectomy, said method comprising administering to a subject in need thereof a therapeutically effective amount of a composition for topical application, said composition 10-30% of an ester of alpha-tocopherol selected from alpha-tocopherol acetate or alpha-tocopherol linoleate and 70-90% of an oily vehicle selected from the group consisting of hydrogenate polyisobutene, hydrogenate polydecene Olus Oil and caprylic/capric triglyceride.

2. A method of treating chronic atrophic rhinitis said method comprising administering to a subject in need thereof a therapeutically effective amount of a composition for topical application, said composition comprising 10-30% of an ester of alpha-tocopherol selected from tocopherol acetate or tocopherol linoleate and 70-90% of an oily vehicle selected from the group consisting of hydrogenate polyisobutene, hydrogenate polydecene Olus oil and caprylic/capric triglyceride.

3. The method according to claim 1, wherein said oily vehicle consists of hydrogenated polydecene.

4. The method according to claim 3, wherein said ester of alpha-tocopherol is alpha-tocopheryl acetate.

5. The method according to claim 1, wherein said composition consists of alpha-tocopheryl acetate and hydrogenated polydecene.

6. The method according to claim 2, wherein said oily vehicle consists of hydrogenated polydecene.

7. The method according to claim 6, wherein said ester of alpha-tocopherol vitamin E is alpha-tocopheryl acetate.

8. The method according to claim 2, wherein said composition consists of alpha-tocopheryl acetate and hydrogenated polydecene.

9. The method according to claim 1, wherein said oily vehicle consists of caprylic/capric triglyceride.

10. The method according to claim 9, wherein said ester of alpha-tocopherol is alpha-tocopheryl acetate.

11. The method according to claim 1, wherein said composition consists of alpha-tocopheryl acetate and caprylic/capric triglyceride.

12. The method according to claim 2, wherein said oily vehicle consists of caprylic/capric triglyceride.

13. The method according to claim 12, wherein said ester of alpha-tocopherol is alpha-tocopheryl acetate.

14. The method according to claim 2, wherein said composition consists of alpha-tocopheryl acetate and caprylic/capric triglyceride.

* * * * *